US007579489B2

(12) United States Patent
Sanborn

(10) Patent No.: US 7,579,489 B2
(45) Date of Patent: Aug. 25, 2009

(54) PROCESSES FOR THE PREPARATION AND PURIFICATION OF HYDROXYMETHYLFURALDEHYDE AND DERIVATIVES

(75) Inventor: Alexandra J. Sanborn, Lincoln, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 11/904,812

(22) Filed: Sep. 28, 2007

(65) Prior Publication Data

US 2008/0027236 A1 Jan. 31, 2008

Related U.S. Application Data

(62) Division of application No. 11/298,014, filed on Dec. 9, 2005, now Pat. No. 7,317,116.
(60) Provisional application No. 60/635,406, filed on Dec. 10, 2004.

(51) Int. Cl.
C07D 307/02 (2006.01)
C07C 51/00 (2006.01)
(52) U.S. Cl. ...................................... 549/488; 562/515
(58) Field of Classification Search ................. 549/488; 562/515
See application file for complete search history.

(56) References Cited

U.S. PATENT DOCUMENTS

| | | | |
|---|---|---|---|
| 2,738,367 A | 3/1956 | Redimon et al. | |
| 2,813,900 A | 11/1957 | Dunlop et al. | |
| 2,917,520 A | 12/1959 | Cope | |
| 2,929,823 A | 3/1960 | Garber et al. | |
| 3,025,307 A | 3/1962 | Garber et al. | |
| 3,040,062 A | 6/1962 | Hales | |
| 3,055,914 A | 9/1962 | Garber et al. | |
| 3,066,150 A | 11/1962 | Jones et al. | |
| 3,071,599 A | 1/1963 | Hales et al. | |
| 3,079,449 A | 2/1963 | Cope | |
| 3,083,236 A | 3/1963 | Utne et al. | |
| 3,118,912 A | 1/1964 | Smith | |
| 3,201,331 A | 8/1965 | Hunter | |
| 3,483,228 A | 12/1969 | Garber et al. | |
| 4,339,387 A | 7/1982 | Fléche et al. | |
| 4,590,283 A * | 5/1986 | Gaset et al. ................. 549/488 | |
| 4,740,605 A | 4/1988 | Rapp | |
| 4,935,530 A | 6/1990 | Lee | |
| 5,608,105 A | 3/1997 | Fitzpatrick | |
| 6,518,440 B2 | 2/2003 | Lightner | |
| 6,706,900 B2 | 3/2004 | Grushin et al. | |
| 6,762,230 B2 | 7/2004 | Brandenburger et al. | |
| 2003/0055271 A1 | 3/2003 | Grushin et al. | |
| 2003/0130528 A1 | 7/2003 | Grushin et al. | |

FOREIGN PATENT DOCUMENTS

| | | | | |
|---|---|---|---|---|
| DE | 632322 | * | 7/1934 | ................. 549/488 |
| DE | 0 360 1281 A1 | | 7/1987 | |
| DE | 19615878 | | 10/1997 | |
| EP | 0 466 409 A1 | | 1/1992 | |
| EP | 0 862 946 A1 | | 9/1998 | |
| FR | 2 663 933 | | 1/1992 | |
| FR | 2 664 273 | | 1/1992 | |
| FR | 2 669 635 | | 5/1992 | |
| FR | 2 669 636 | | 5/1992 | |
| FR | 2 670 209 | | 6/1992 | |
| GB | 0838957 A | | 6/1960 | |
| GB | 0887360 A | | 1/1962 | |
| GB | 0888568 A | | 1/1962 | |
| JP | 55053280 | | 4/1980 | |
| RU | 2203279 | * | 4/2003 | ................. 549/488 |
| WO | WO 03/024947 | | 3/2003 | |
| WO | WO 2005/018799 A1 | | 3/2005 | |

OTHER PUBLICATIONS

Tarabanko et al. STN Accession No. 2003:99382; Abstract of Khimiya Rastitel'nogo Syr'ya (2002), (2), 5-15, 1029-5151.*
Brown et al. STN Accession No. 1983:200176, Abstract of Journal of Chemical Technology and Biotechnology, 1982, 32(10), 920-4.*
Lichtenthaler et al Liebigs Annalen der Chemie (1993), (9), 967-74.*
Brochure entitled "Catalysts and Applications of the Chemical Specialties Business Unit," Süd-Chemie Inc., pp. 1, 2, 6, 17, 19-21.
Halliday, Gary A., Robert J. Young, and Vladimir V. Grushin. "One-Pot, Two-Step, Practical Catalytic Synthesis of 2,5-Diformylfuran from Fructose." *Organic Letters* 5 (2003), No. 11, 3pp.
Herring, Andrew M., J. Thomas McKinnon, David E. Petrick, Keith W. Gneshin, Jonathan Filley, and Bryan D. McCloskey ."Detection of reactive intermediates during laser pyrolysis of cellulose char by molecular beam mass spectroscopy, implications for the formation of polycyclic aromatic hydrocarbons." *Journal of Analytical and Applied Pyrolysis*. 66 (2003), pp. 165-182.
Lichtenthaler, Frieder W. "Unsaturated O- and N—Heterocycles from Carbohydrate Feedstocks." *Accounts of Chemical Research*. vol. 35, No. 9. 2002, pp. 728-737.
Lewkowski, Jaroslaw. "Synthesis, Chemistry and Applications of 5-Hydroxymethyl-furfural And Its Derivatives." *Department of Organic Chemistry, University of Lodz, Narutowicza* 68, 90-136, Lodz, Poland. pp. 17-54.
Kröger, Martin, Ulf Pruβe and Klaus-Dieter Vorlop. "A new approach for the production of 2,5-furandicarboxylic acid by in situ oxidation of 5-hydroxymethylfurfural starting from fructose." *Topics in Catalysis* 13 (2000), pp. 237-242.
Spyroudis, Spyros. "Hydroxyquinones: Synthesis and Reactivity." *Molecules* 2000, pp. 1291-1330.
Tyrlik, Stanislaw K., Dorota Szerszeń, Marian Olejnik, and Witold Danikiewicz. "Selective dehydration of glucose to hydroxymethylfurfural and a one-pot synthesis of a 4-acetylbutyrolactone from glucose and trioxane in solutions of aluminum salts." *Carbohydrate Research* 315 (1999), pp. 268-272.

(Continued)

Primary Examiner—D. Margaret Seaman
Assistant Examiner—Nizal S Chandrakumar
(74) Attorney, Agent, or Firm—K & L Gates LLP

(57) ABSTRACT

A method for utilizing an industrially convenient fructose source for a dehydration reaction converting a carbohydrate to a furan derivative is provided. Recovery methods also are provided. Embodiments of the methods improve upon the known methods of producing furan derivatives.

9 Claims, No Drawings

OTHER PUBLICATIONS

Moreau, Claude, Robert Durand, Delphine Peyron, Jean Duhamet, and Patrick Rivalier. "Selective preparation of furfural from xylose over microporous solid acid catalysts." *Industrial Crops and Products.* 7 (1998), pp. 95-99.

Lichtenthaler, Frieder W. "Towards improving the utility of ketoses as organic raw materials." *Carbohydrate Research.* 313 (1998), pp. 69-89.

Gandini, Alessandro, and Mohamad Naceur Belgacem. "Furans in Polymer Chemistry" *Prog. Polym. Sci.* vol. 22, 1997, pp. 1203-1379.

Moreau, Claude, Robert Durand, Cécile Pourcheron, and Sylvie Razigade. "Preparation of 5-hydroxymethylfurfural from fructose and precursors over H-form zeolites." *Industrial Crops and Products.* 3 (1994) pp. 85-90.

Lourvanji, Khavinet, and Gregory L. Rorrer. "Dehydration of glucose to organic acids in microporous pillared clay catalysts." *Applied Catalysis A:General* 109 (1994), pp. 147-165.

A. Fuchs, Ed. "Inulin and Inulin-containing Crops." *Studies in Plant Science* 3 (1993), pp. 149-160.

Vinke, P., and H. van Bekkum. "The Dehydration of Fructose Towards 5-Hydroxymethylfurfural Using Activated Carbon as Adsorbent." *Starch/starke* 44 (1992) No. 3, pp. 90-96.

Sanda, Komla, Luc Rigal and Antoine Gaset. "Optimisation of the Synthesis of 5-Chloromethyl-2-furancarboxaldehyde from D-Fructose Dehydration and in-situ Chlorination of 5-Hydroxymethyl-2-furancarboxaldehyde." *Journal of Chemical Technology, Biotechnol.* 0268-2575/92, pp. 139-145.

Chen, Ji-Dong, Ben F.M. Kuster, and Kees Van Der Wiele. "Preparation of 5-Hydroxymethylfurfural via Fructose Acetonides in Ethylene Glycol Dimethyl Ether." *Biomass and Bioenergy* vol. 1 No. 4, pp. 217-223.

Antal, Michael Jerry and William S. L. Mok. Geoffrey N. Richards. "Mechanism of formation of 5-(hydroxymethyl)-2-furaldehyde from D-fructose sucrose." *Carbohydrate Research.* 199 (1990) pp. 91-109.

Musau, Richard M. and Raphael M. Munavu. "The Preparation of 5-Hydroxymethyl-2-Furaldehyde (HMF) from D-Fructose in the Presence of DMSO." *Biomass* 13 (1987), pp. 67-74.

Jow, Jinder, Gregory L. Rorrer and Martin C. Hawley. "Dehydration of D-Fructose to Levulinic Acid over LZY Zeolite Catalyst." *Biomass* 14 (1987) pp. 185-194.

Van Dam, H.E., P.P.G. Kieboom and H. van Bekkum. "The Conversion of Fructose and Glucose in Acidic Media: Formation of Mydroxymethylfurfural." *Starch/starke* 38 (1986) No. 3, pp. 95-101.

Jogia, Madhu K., Veikila Vakamoce and Rex T. Weavers. "Synthesis of Some Furfural and Syringic Acid Derivatives." *Aust. J. Chem.*, 1985, 38, pp. 1009-1016.

Hamada, Kazuhiko, Hiroshi Yoshihara, Gohfu Suzukamo and Osamu Hiroaki. "The Dehydration of Ketohexoses into 5-Chloromethyl-2-furaldehyde. The Isolation of Diketohexose Dianhydrides." *Bull. Chem. Soc. Jpn.* 57, 1984, pp. 307-308.

Brown, David W., Arthur J. Floyd, Richard G. Kinsman and Yusuf Roshan-Ali. "Dehydration Reactions of Fructose in Non-aqueous Media." *J. Chem. Biotechnol.* 1982, 32, pp. 920-924.

Szmant, H. Harry and Deena D. Chundury. "The Preparation of 5-Hydroxymethylfurfuraldehyde from High Fructose Corn Syrup and Other Carbohydrates." *J. Chem. Tech. Biotechnol.* 1981, 31, pp. 135-145.

Mercadier, Daniel, Luc Rigal, Antoine Gaset and Jean-Pierre Gorrichon. "Synthesis of 5-Hydroxymethyl-2-furancarboxaldehyde Catalysed by Cationic Exchange Resins. Part 2. Analysis and Discussion of the Effect of the Main Parameters on the HMF Output." *J. Chem. Tech. Biotechmol.* 1981, 31, pp. 497-502.

Mercadier, Daniel, Luc Rigal, Antoine Gaset and Jean-Pierre Gorrichon. "Synthesis of 5-Hydroxymethyl-2-furancarboxaldehyde Catalysed by Cationic Exchange Resins. Part 1. Choice of the Catalyst and the Characteristics of the Reaction Medium." *J. Chem. Tech. Biotechmol.* 1981, 31, pp. 489-496.

Mercadier, Daniel, Luc Rigal, Antoine Gaset and Jean-Pierre Gorrichon. "Synthesis of 5-Hydroxymethyl-2-furancarboxaldehyde Catalysed by Cationic Exchange Resins. Part 3. Kiunetic Approach of the D-Fructose Dehydration." *J. Chem. Tech. Biotechmol.* 1981. 31. pp. 503-508.

Rigal, Luc, Antoine Gaset, and Jean-Pierre Gorrichon. "Selective Conversion of D-Fructose to 5-Hydroxymethyl-2-furancarboxaldehyde Using a Water-Solvent-Ion-Exchange Resin Triphasic System." *Ind. Eng. Chem. Prod. Res. Dev.*(1981), No. 4, pp. 719-721.

Chundury, D. and H.H. Szmant. "Preparation of Polymeric Building Blocks from 5-Hydroxymethyl-and 5-Chloromethylfurfuraldehyde." *Ind. Eng. Chem. Prod. Res. Dev.* 20 (1981), No. 1, pp. 158-163.

Rekker, Roelof F. and Hubertus M. De Kort. "The hydrophobic fragmental constant; an extension to a 1000 data point set." *Eur. J. Med. Chem.* Nov.-Dec. 1979-14 No. 6, pp. 479-488.

Kuster, B.F.M. and J. Laurens. "Preparation of 5-Hydroxymethylfurfural." *Die Starke* 29. 1977 No. 5, pp. 172-176.

Kuster, Ben F.M. and Leo M Tebbens. "Analytical Procedures for Studying the Dehydration of D-Fructose." *Carbohydrate Research* 54 (1977), pp. 159-164.

Kuster, B.F.M. and H.J.C. van der Steen. "Preparation of 5-Hydroxymethylfurfural." *Die Starke* 29, No. 3, pp. 99-103.

Kuster, Ben F.M. and Hessel S. van der Baan. "The Influence of the Initial and Catalyst Concentrations on the Dehydration of D-Fructose." *Carbohydrate Research.* 54 (1977), pp. 165-176.

Kuster, Ben F.M. and Herman M.G. Temmink. "The Influence of pH and Weak-Acid Anions on the Dehydration of D-Fructose." *Carbohydrate Research.* 54 (1977), pp. 185-191.

Leo, Albert, Corwin Hansch and David Elkins. Albert Leo. "Partition Coefficients and their Uses." *Chemical Reviews.* vol. 71. No. 6 Dec. 1971. pp. 525-554, 586-603, 604-605, 555-585, 606-616.

Brady, Jr., Robert F. "Cyclic Acetals of Ketoses." *Carbohydrate Research* 15 (1970), pp. 35-40.

Moye, C.J. and R.J. Goldsack. "Reaction of Ketohexoses with Acid in Certain Non-Aqueous Sugar Solvents." *J. Appl. Chem.*, 1966. vol. 16 July, pp. 206-208.

Wolfrom, Melville L. Ed. "Advances in Carbohydrate Chemistry." *Academic Press* New York and London. 1964, pp. 181-218.

Bonner, T.G., E.J. Bourne and M. Ruszkewicz. "The Iodine-catalysed Conversion of Sucrose into 5-Hydroxymethylfurfuraldehyde." *Journal of The Chemical Society*, Jan. 1960, pp. 787-791.

Cottier, Louis, Gérard Descotes, Jaroslaw Lewkowski, Romuald Skrowroñski and Estelle Viollet, "Oxidation of 5-Hydroxymethylfurfural and Derivatives to Furanaldehydes with 2,2,6,6-Tetramethylpiperidine Oxide Radical—Co-oxidant Pairs," *J. Heterocyclic Chem.*, vol. 32, 1995, pp. 927-930.

Cope, Arthur C. and Warren N. Baxter, "Aminoalcohols Containing the 8-Oxa-3-azabicyclo[3.2.1]octane Ring System and Their Benzoates", (*journal title unknown—contribution from the Department of Chemistry, Massachusetts Institute of Technology*) 77 (1955), pp. 393-396.

Turner, James H. Paul A. Rebers, Paul L. Barrick, and Robert H. Cotton, "Determination of 5-(Hydroxymethyl)-2-furaldehyde and Related Compounds", *Analytical Chemistry* 26 (1954), No. 5, pp. 898-901.

Timko, Joseph M., Stephen S. Moore, David M. Walba, Philippe C. Hiberty, and Donald J. Cram, "Host-Guest Complexation. 2. Structural Units That Control Association Constants Between Polyethers and *tert*-Butylammonium Salts", *Journal of the American Chemical Society* 99:13 (1977), pp. 4207-4219.

Brochure entitled "Future Perspectives", Süd-Chemie Inc. (2006) 5 pages.

Kuster, B.F.M., "5-Hydroxymethylfurfural (HMF). A Review Focussing on its Manufacture", *Starch/Stärke* 42 (1990), No. 8, pp. 314-321.

Bobbitt, James M. and M. Cecile L. Flores, "Organic Nitrosoium Salts as Oxidants in Organic Chemistry", *Heterocycles* 27 (1988), No. 2, pp. 509-533.

Haworth, W.N., W.G.M. Jones, and L.F. Wiggins, "The Conversion of Sucrose into Furan Compounds. Part II. Some 2:5-Disubstituted Tetrahydrofurans and their Products of Ring Scission", *Journal of the Chemical Society* (1945), pp. 1-4.

Einhorn, Jacques, Cathy Einhorn, Fabien Ratajczak, and Jean-Louis Pierre, "Efficient and Highly Selective Oxidation of Primary Alcohols to Aldehydes by N-Chlorosuccinimide Mediated by Oxoammonium Salts", *J. Org. Chem.* 61 (1996), pp. 7452-7454.

Bobbitt, James M., "Oxoammonium Salts. 6. 4-Acetylamino-2,2,6,6-tetramethylpiperidine-1-oxoammonium Perchlorate: A Stable and Convenient Reagent for the Oxidation of Alcohols. Silica Gel Catalysis", *J. Org. Chem.* 63 (1998), pp. 9367-9374.

Moore, J.A. and J.E. Kelly, "Polyesters Derived from Furan and Tetrahydrofuran Nuclei", *Macromolecules* 11 (1978), No. 3, pp. 568-573.

Meuser, Friedrich, Norbert Gimmler and Kens Oeding, "Systemanalytische Betrachtung der Derivatisierung von Stärke mit einem Kochextruder als Reaktor", *Starch/Stärke* 42 (1990), No. 9, pp. 330-336 (English abstract).

de Nooy, Arjan E.J., Arie C. Besemer, and Herman van Bekkum, "On the Use of Stable Organic Nitroxyl Radicals for the Oxidation of Primary and Secondary Alcohols", *Synthesis* (1996), pp. 1153-1174.

Leo, A., C. Hansch, and D. Elkins, "Partition Coefficients and Their Uses", *Chemical Reviews* 71 (1971), No. 6 p. 525, pp. 555-605.

"MP-TsO-TEMPO", Argonaut Technologies Inc., Technical Note 509, pp. 1-8.

De Luca, Lidia, Giampaolo Giacomelli, Simonetta Masala, and Andrea Porcheddu, "Trichloroisocyanuric/TEMPO Oxidation of Alcohols under Mild Conditions: A Close Investigation." *Journal of Organic Chemistry* 68(12) (2003), pp. 4999-5001 (abstract only).

Drury, J.S., "Miscibility of solvent pairs", *Industrial and Engineering Chemistry* 44(11); pC-684.

Hansch, C. and Leo, A., "Substituent Constants for Correlation Analysis in Chemistry and Biology", John Wiley & Sons, New York, NY (1979).

Written Opinion of the International Searching Authority, European Patent Office, Nov. 7, 2006, 11pp.

Benvenuti, F. et al. "Heterogeneous zirconium and titanium catalysts for the selective synthesis of 5-hydroxymethyl-2-furaldehyde from carbohydrates." *Applied Catalysis, A: General* 193 (1,2) (2000), pp. 147-153.

Bicker, M. et al. "Dehydration of fructose to 5-hydroxymethylfurfural in sub- and supercritical acetone." *Green Chemistry* 5(2) (2003), pp. 280-284.

Fayet, C. et al. "Nouvelle méthode de préparation du 5-dehydroxyméthyl-2-furaldéhyde par action de sels d'ammonium ou d'immonium sur les mono-, olido- et poly-saccharides. Accès direct aux 5-halogénométhyl-2-furaldéhydes." *Carbohydrate Research* 122 (1983), pp. 59-68 (English abstract).

Grin, S.A. et al. "Character of acid catalysis in the dehydration of fructose with formation of 5-(hydroxymethyl) furfural." *Khimicheskaya Fizika* 13(5) (1994), pp. 113-118 (abstract in English).

Nakamura, Yoshio. "Preparation of 5-(hydroxymethyl) furfural by selective dehydration of D-fructose." XP002398128 retrieved from STN Database accessIon No. 1981:156646, Chemical Abstracts Service, Columbus, OH (1981) (English abstract only).

Ribeiro, Marcelo L. et al. "Synthesis of 2,5-furandicarboxylic acid from fructose: a suitable precursor for biopolymers." *Natural Polymers and Composites IV*, Proceedings from the International Symposium on Natural Polymers and Composites, 4th, Sao Pedro, Brazil, Sep. 1-4, 2002, pp. 192-197.

Yadav, Ganapati D. et al. "Selectivity engineering in conversion of sugars into 5-hydroxymethylfurfuraldehyde." *Abstracts of Papers*, 227th ACS National Meeting, Anaheim, CA, United States, Mar. 28-Apr. 1, 2004, Cell-063.

Romén-Leshkov, Y et al. "Production of dimethylfuran for liquid fuels from biomass-derived carbohydrates." *Nature* 47 (Jun. 21, 2000), pp. 982-986.

Román-Leshkov, Y et al. "Phase Modifiers Promote Efficient Production of Hydroxymethylfurfural from Fructose." *Science* 312 (Jun. 30, 2006), pp. 1933-1937.

* cited by examiner

PROCESSES FOR THE PREPARATION AND PURIFICATION OF HYDROXYMETHYLFURALDEHYDE AND DERIVATIVES

CROSS-REFERENCE TO RELATED APPLICATIONS

The present application claims priority to and incorporates by reference U.S.Provisional Application No. 60/635,406, filed Dec. 10, 2004 and U.S. patent application Ser. No. 11/070,063, filed Mar. 2, 2005. This application is a division of co-pending U.S. application Ser. No. 11/298,014, filed Dec. 9, 2005, now U.S. Pat. No. 7,317,116 which is incorporated by reference herein in its entirety.

FIELD OF THE INVENTION

Improved methods of producing chemical compounds are included herein. The dehydration reaction of common carbohydrates to form commercially important compounds, furan derivatives, and methods of optimizing the reactions to efficiently synthesize the products, as well as improved methods of purification are included herein.

BACKGROUND OF THE INVENTION 2,5-(Hydroxymethyl)furaldehyde, also known as 2,5-(hydroxymethyl)furfural (HMF), has many important industrial and commercial applications, largely due to its many functional groups and ability to serve as a precursor in many polymerization reactions. HMF, for example, is a suitable starting source for the formation of various furan monomers required for the preparation of non-petroleum-derived polymeric materials. HMF, as well as other 2,5-disubstituted furanic derivatives, also has great potential for use in the field of intermediate chemicals from regrowing resources. Also due to its various functionalities, HMF may be used to produce a wide range of products, including, but not limited to, polymers, solvents, surfactants, pharmaceuticals, and plant protecting agents. HMF is shown in the structure below:

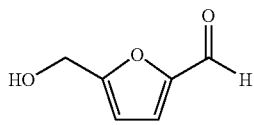

The use of HMF and other furfural derivatives may be compared with the use of corresponding benzene-based macromolecular compounds. In order to be cost-effective and compete in this market, HMF must be able to be produced at competitive prices. The production of HMF has been studied for years, but an efficient and cost-effective method of producing HMF in high yields has yet to be found. HMF is primarily produced from the dehydration reaction of a carbohydrate compound, particularly monosaccharides, including glucose and fructose. Complications arise from the rehydration of HMF after the dehydration occurs, which often yields the by-products of levulinic acid, and formic acid. Another competing side reaction is the polymerization of HMF and/or fructose to form humin polymers.

Hexoses are the preferred carbohydrate source from which HMF is formed. Fructose is the preferred hexose used for the dehydration reaction to form HMF. This is in part because fructose has been shown to be more amendable to the dehydration reaction to a form HMF. Fructose is shown by the structures below:

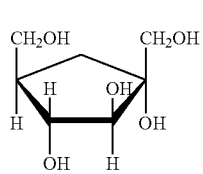 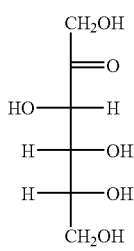

Fructose however, is more expensive than other hexoses, such as glucose (dextrose), and maltose, for example. Early processes and procedures for the production of HMF concentrated on the use of crystalline fructose, but its widespread use is prevented by its high cost. Other sources of fructose, including high-fructose corn syrup (HFCS), have been used to produce HMF and other furan derivatives. Szmant and Chundury used high fructose corn syrup as a starting material in forming HMF, as disclosed in a 1981 article in *J. Chem. Tech. Biotechnol.*, 31, (pgs. 135-145). Szmant uses a variety of carbohydrates as starting material, but designs reaction conditions specific to each fructose source. Szmant, for example, uses a boron trifluoride catalyst ($BF_3Et_2O$) with DMSO as a solvent in the conversion of HFCS to HMF, but utilizes different catalyst/solvent combinations with different starting materials. Use of $BF_3Et_2O$ as a catalyst is not economically practical since it cannot be recovered and re-used. Furthermore, Szmant requires the use of a Pluronic emulsifier to suppress foaming. Szmant also requires bubbling of nitrogen to suppress oxidation. Still further, Szmant requires the use of DMSO as a solvent, which is not easily separable from the HMF product, and therefore creates difficulties with product recovery. It is very desirable, therefore, to develop an industrially practicable process for producing HMF in high purity.

U.S. Pat. No. 6,706,900 to Grushin et al. (Grushin '900) also discloses the dehydration of fructose in the form of high-fructose corn syrup, to form HMF as an intermediate; but this process is performed in the context of forming diformylfuran, also known as 2,5-dicarboxaldehyde (DFF). The reaction proceeds in an aqueous environment, and the HMF that is formed is not isolated from the reaction mixture, but rather is directly converted to DFF without an isolation step. The reaction conditions of Grushin '900 are therefore not constrained by considerations of product yields of HMF, as it is formed as an intermediate that is not isolated as a product. More importantly from a practical commercial standpoint, Grushin '900 is not constrained by considerations of isolating HMF from the product mixture. An efficient method for producing HMF in desirable yields and sufficiently high purity from a natural and industrially convenient fructose source that may include other mixed carbohydrates has yet to be found.

Water has in the past been used as a solvent of choice in dehydration reactions forming HMF because of the solubility of fructose in water. Aqueous conditions, however, have proven to deleteriously affect the dehydration reaction of fructose to HMF in a variety of ways. Aqueous conditions have led to decreased yield of HMF as low selectivity for the dehydration reaction has been demonstrated. Furthermore, solvation of protons in water highly reduces the catalytic activity for the dehydration reaction. Low selectivity of the dehydration reaction simultaneously leads to increased polymerization reactions and humin formation, which also interfere with the synthesis of HMF.

In an attempt to solve such problems associated with aqueous systems, one proposed solution involves an improvement by simultaneously extracting HMF after the dehydration reaction. A similar attempt to improve yields involves the adsorption of HMF on activated carbon. The key factor in these processes is a rapid removal of HMF from the acidic medium in which it is formed. However, these systems generally suffer from high dilution or partially irreversible adsorption of HMF.

In another attempt to solve the problems of aqueous systems, an organic solvent may be added to the aqueous solution, such as, for example, butanol or dioxane. Such systems, however, present a difficulty in that rehydration of HMF is common and ether formation of HMF occurs with the solvent if alcohols are employed. High yields of HMF, therefore, were not found with the addition of these organic solvents. In a further attempt to provide an adequate solvent system, aqueous solvent mixtures and anhydrous organic solvents have also been employed to ensure favorable reaction conditions. Examples of anhydrous organic solvents used include dimethylformamide, acetonitrile, dimethylsulfoxide, and polyethylene glycol.

Dimethylsulfoxide (DMSO), for example, has been extensively studied and employed as a solvent in the dehydration reaction to form HMF. Improved yields of HMF have been reached with ion exchangers or boron trifluoride etherate as a catalyst, and even without any catalyst. DMSO presents a problem, however, in that recovery of HMF from the solvent is difficult.

Furthermore, although dehydration reactions performed in solvents with high boiling points, such as dimethylsulfoxide and dimethylformamide, have produced improved yields, the use of such solvents is cost-prohibitive, and additionally poses significant health and environmental risks in their use. Still further, purification of the product via distillation has not proven effective for a variety of reasons. First of all, on long exposure to temperatures at which the desired product can be distilled, HMF and impurities associated with the synthetic mixture tend to be unstable and form tarry degradation products. Because of this heat instability, a falling film vacuum still must be used. Even in use with such an apparatus however, resinous solids form on the heating surface causing a stalling in the rotor, and the frequent shutdown resulting therefrom makes the operation inefficient.

Catalysts may also be used to promote the dehydration reaction. Some commonly used catalysts include cheap inorganic acids, such as $H_2SO_4$, $H_3PO_4$, HCl, and organic acids such as oxalic acid, levulinic acid, and p-toluene sulfonic acid. These acid catalysts are utilized in dissolved form, and as a result pose significant difficulties in their regeneration and reuse, and in their disposal. In order to avoid these problems, solid sulfonic acid catalysts have also been used. Solid acid resins, however, are limited in use by the formation of deactivating humin polymers on their surfaces under conditions taught by others. Other catalysts, such as boron trifluoride etherate, can also be used. Metals, such as Zn, Al, Cr, Ti, Th, Zr, and V can be used as ions, salts, or complexes as catalysts. Such use has not brought improved results, however, as yields of HMF have continued to be low. Ion exchange catalysts have also been used, but have also delivered low HMF yields under conditions taught by others, and further limit the reaction temperature to under 130° C.

SUMMARY OF THE INVENTION

Provided herein is an improved method of preparing 2,5-(hydroxymethyl)furaldehyde comprising: i) combining a fructose source, a solvent selected from the group consisting of 1-methyl-2-pyrrolidinone, dimethylacetamide, dimethylformamide and combinations of thereof, with a catalyst to provide a reaction mixture; ii) heating said reaction mixture to a temperature and for a time sufficient to promote an acid-catalyzed dehydration reaction of fructose in said fructose source to form a product mixture; and iii) isolating 2,5-(hydroxymethyl)furaldehyde from said product mixture.

In another embodiment, there is provided a method of preparing 2,5-(hydroxymethyl)furaldehyde comprising: i) combining a fructose source, an organic solvent, and an acid catalyst to provide a reaction mixture; ii) heating said reaction mixture to a temperature and for a time sufficient to promote a dehydration reaction of fructose in said fructose source to form a first product mixture; iii) neutralizing the pH of the first product mixture to a pH of about 7 to 9; iv) distilling the first product mixture after neutralizing the pH to remove said organic solvent remaining in the first product mixture; and v) purifying said product mixture to provide a second product mixture comprising greater than 60% by weight of 2,5-(hydroxymethyl)furaldehyde.

Also provided also herein is a method of preparing 2,5-(hydroxymethyl)furaldehyde comprising the steps of: i) combining a fructose source, an acid catalyst, a first organic solvent, and a second organic solvent that is non miscible with the first organic solvent to provide a reaction mixture, the first and second organic solvents being selected so that the second organic solvent preferentially dissolves 2,5-(hydroxymethyl) furaldehyde relative to the first organic solvent; ii) heating said reaction mixture to a temperature and for a time sufficient to promote a dehydration reaction of fructose in said fructose source to form a product mixture with a first immiscible phase and a second immiscible phase; and iii) isolating 2,5-(hydroxymethyl)furaldehyde from said second immiscible phase of said product mixture.

In another embodiment, provided herein is a method of preparing an R-oxymethylfurfural ether of hydroxylmethylfurfural of the formula:

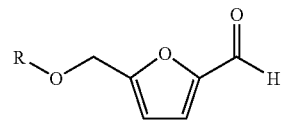

where R is selected from the group consisting of alkyl, cycloalkyl, allyl and aryl, comprising: (i) combining a fructose source, an R—OH solvent, and an acid catalyst to form a reaction mixture; (ii) heating said reaction mixture to a temperature and for a time sufficient to promote an acid-catalyzed dehydration reaction fructose in the fructose source and to form R-oxymethylfurfural in a product mixture; and (iii) Isolating the R-oxymethylfurfural from said product mixture.

Also provided herein is a method of preparing levulinic acid comprising: (i) combining a fructose source, at least one of polyethylene glycol and end capped polyethylene glycol, and an acid catalyst to form a reaction mixture; (ii) heating said reaction mixture to a temperature and for a time sufficient to promote an acid-catalyzed dehydration reaction of fructose in the fructose source and to form levulinic acid in a product mixture; and (iii) isolating levulinic acid from said product mixture.

In another embodiment, provided herein is a method of preparing 2,5-bis-(hydroxymethyl)furan comprising: heating a reaction mixture comprising 2,5-(hydroxymethyl)furaldehyde, a solvent, and a catalyst system comprising nickel and zirconium at a temperature, for a time, and at a pressure sufficient to promote reduction of the 2,5-(hydroxymethyl) furaldehyde to 2,5-bis-(hydroxymethyl)furan to produce a product mixture comprising 2,5-bis-(hydroxymethyl)furan.

Provided herein is an improved method of preparing 2,5-(hydroxymethyl)furaldehyde. The method includes the steps of: i) combining materials comprising a fructose source, a solvent, and a catalyst to form a reaction mixture; ii) heating said reaction mixture to a temperature and for a time sufficient to promote an acid-catalyzed dehydration reaction of fructose in said fructose source to form a product mixture; and iii) isolating 2,5-(hydroxymethyl)furaldehyde from said product mixture. Preferably the catalyst is a heterogeneous, re-usable, or recyclable catalyst.

In one embodiment the fructose source is high fructose corn syrup, and the method is performed under vacuum conditions. In a further embodiment the carbohydrate source is added gradually in a stepwise fashion once the reaction has been initiated, this entails the addition of two or more discrete aliquots over a specified period of time. In an additional embodiment, the mixed carbohydrate source comprises a first carbohydrate source in a first physical state, and a second carbohydrate source in a second physical state, wherein the first and second physical states are not the same, that is to say they are in different physical states. Suitable carbohydrate sources include, but are not limited to, a hexose, a pentose, fructose syrup, crystalline fructose, and, process streams from the crystallization of fructose.

Suitable mixed carbohydrate source may comprise any industrially convenient carbohydrate sources, such as corn syrup. The mixed carbohydrate sources include, but are not limited to, hexoses, fructose syrup, crystalline fructose, high fructose corn syrup, crude fructose, purified fructose, high fructose corn syrup refinery intermediates and by-products, process streams from crystallizing fructose or glucose, and molasses, such as soy molasses resulting from production of soy protein concentrate.

Provided also herein is a further method of preparing 2,5-(hydroxymethyl)furaldehyde that includes the steps of: i) combining materials comprising a carbohydrate source, an organic solvent, and an ion-exchange resin catalyst to form a non-aqueous reaction mixture; ii) heating said non-aqueous reaction mixture to a temperature and for a time sufficient to promote a dehydration reaction of said carbohydrate source to form a first product mixture; iii) removing the ion-exchange resin catalyst from the first product mixture to provide a product isolate; iv) distilling the product isolate to remove said solvent remaining in said product isolate; and v) purifying said product isolate to provide a second product mixture comprising greater than 60% by weight of 2,5-(hydroxymethyl)furaldehyde. In one embodiment, the product isolate is adjusted to a neutral pH after removing the ion-exchange resin from said product mixture, and before being subjected to a distillation to remove the organic solvent.

In one embodiment, the product mixture may be further isolated by such methods which are well known in the art, such as, but not limited to, filtration, vacuum or suction filtration, or gravity filtration. Purification of the product isolate may be carried out by a solvent extraction process to provide the second product mixture. Examples of solvent extraction processes that may be used include, but are not limited to, a column chromatography process and liquid-liquid extraction. A liquid-liquid extraction process comprises adding a mixture of a water-immiscible organic solvent and water to the product isolate to form an organic phase and an aqueous phase. This is followed by recovering the organic phase, and removing the water-immiscible solvent to yield purified 2,5-(hydroxymethyl) furaldehyde.

The possible extracting solvents include, but are not limited to, ethyl acetate, methyl isobutylketone, methyl ethyl ketone, methyl t-butyl ether, ethyl lactate, octanol, pentanol, and butyl acetate and combinations thereof. In a certain embodiment, the second product mixture comprises greater than 75% by weight of 2,5-(hydroxymethyl)furaldehyde. Yet another embodiment, the second product mixture comprises greater than 95% by weight of 2,5-(hydroxymethyl)furaldehyde.

In one embodiment, after product isolation the ion-exchange resin catalyst may be rinsed with the organic solvent used to carry out the reaction to recover product contained within the resin. After the rinse, the ion-exchange resin catalyst may be reused in a subsequent reaction. In a further embodiment, after product isolation the ion-exchange resin may be rinsed with a second organic solvent to recover product contained with in the resin. After the rinse, the ion-exchange resin catalyst may be reused in a subsequent reaction.

Provided also herein is a further method of preparing 2,5-(hydroxymethyl)furaldehyde. The method includes: i) combining materials comprising a carbohydrate source, a solvent and an ion-exchange resin catalyst to form a reaction mixture; ii) heating the reaction mixture to a temperature and for a time sufficient to promote a dehydration reaction of said carbohydrate source to form a first product mixture; iii) isolating the first product mixture to provide a product isolate. The method optionally comprises one or more of the following steps: iv) adjusting the product isolate to a neutral pH; v) adding a non-volatile flowing agent to the product isolate; vi) distilling the non-volatile flowing agent and the product isolate to remove the solvent from the product isolate; and vii) purifying the product isolate to provide a second product mixture comprising greater than 75% by weight of 2,5-(hydroxymethyl)furaldehyde.

In an embodiment, the purification of the product isolate may be performed by a process selected from the group consisting of short path distillation, thin film evaporation, wiped film evaporation, crystallization, and adsorption to an inert adsorbent. Adsorbents include, but are not limited to, silica, carbon, alumina, and other resins. A non-volatile flowing agent may be added to the product isolate to enhance separation. The non-volatile flowing agent may be chosen from the group consisting of polyethylene glycol, polyethylene glycol monoether, polyethylene glycol diether, and combinations thereof. In a further embodiment, the non-volatile flowing agent may be purified to a re-usable form after it has performed its role in the purification process. Such purification process may take place with the use of carbon as disclosed herein.

Provided also herein is a further method of preparing 2,5-(hydroxymethyl)furaldehyde. The method includes: i) combining materials comprising a carbohydrate source, a catalyst, a first organic solvent, and a second organic solvent to form a non-aqueous reaction mixture wherein said first organic solvent and said second organic solvent are immiscible in each other; ii) heating the non-aqueous reaction mixture to a temperature and for a time sufficient to promote a dehydration reaction of the carbohydrate source in said first organic solvent to form a product mixture with a first immiscible phase and a second immiscible phase; and iii) isolating 2,5-(hydroxymethyl)furaldehyde from said second immiscible phase of said product mixture.

In one embodiment of the above method, the second organic solvent is characterized by an ability to solubilize HMF in the presence of the first organic solvent, which is immiscible with regard to the second organic solvent and HMF. The second organic solvent may be selected from the group including, but not limited to, methyl isobutyl ketone, ethyl acetate, and chloroform. The first organic solvent is characterized as being less able to solubilize HMF than the second organic solvent when in contact with the second organic solvent; the result of which is a two-phase system. HMF is less soluble in said first immiscible organic phase than in said second immiscible organic phase. In one embodiment, the first organic solvent is dimethyl formamide.

Provided also herein is a method of preparing 2,5-bis-(hydroxymethyl)furan. The method includes heating a reaction mixture comprising 2,5-(hydroxymethyl)furaldehyde, a solvent, and a catalyst system comprising nickel and zirconium at a temperature, for a time, and at a pressure sufficient to promote reduction of the 2,5-(hydroxymethyl)furaldehyde to 2,5-bis-(hydroxymethyl)furan to produce a product mixture comprising 2,5-bis-(hydroxymethyl)furan.

In one embodiment, the method provides that greater than 90% of the 2,5-(hydroxymethylfuraldehyde) is converted to 2,5-bis-(hydroxymethyl)furan. In another embodiment, greater than 95% of the 2,5-(hydroxymethylfuraldehyde) is converted to 2,5-bis-(hydroxymethyl)furan, and in yet a further embodiment, greater than 99% of the 2,5-(hydroxymethylfuraldehyde) is converted to 2,5-bis-(hydroxymethyl)furan.

In an embodiment, the method takes place with a temperature which is between about 125° C. and about 175° C. In another embodiment, the method takes place with a temperature which is between about 140° C. and about 160° C. In an embodiment, the pressure is between about 1,000 pounds per square inch and about 1,400 pounds per square inch. In another embodiment, the pressure is between about 1050 pounds per square inch and about 1,250 pounds per square inch.

In an embodiment, the time sufficient to promote reduction of the 2,5-(hydroxymethyl)furaldehyde to 2,5-bis-(hydroxymethyl)furan is less than about three hours. In another embodiment, the time sufficient to promote reduction of the 2,5-(hydroxymethyl)furaldehyde to 2,5-bis-(hydroxymethyl)furan is less than about two hours. In a further embodiment, the time sufficient to promote reduction of the 2,5-(hydroxymethyl)furaldehyde to 2,5-bis-(hydroxymethyl)furan is about one hour.

In an embodiment, the method of preparing 2,5-bis-(hydroxymethyl)furan further includes isolating 2,5-bis-(hydroxymethyl)furan from the product mixture by filtration to remove the catalyst and rotary evaporation to remove the solvent. In an embodiment, the solvent is one of ethyl acetate, acetate, methyl acetate, butyl acetate, isopropanol, and butanol. In another embodiment, the reaction mixture comprising 2,5-(hydroxymethyl)furaldehyde is a crude reaction mixture.

DETAILED DESCRIPTION OF THE INVENTION

Reusable or recyclable catalysts are preferred for use in the reaction, as they provide for increased efficiency, and economic and industrial feasibility. As used herein, the term "recyclable catalyst" refers to a catalyst which is not irreversibly expended as a result of the reaction. In other words, the catalyst may be used again. Examples of recyclable or reusable catalysts include, but are not limited to, solid acid catalysts, ion-exchange resins, zeolites, Lewis acids, clays, and molecular sieves. Solid acid catalysts often comprise a solid material which has been functionalize to impart acid groups that are catalytically active. Solid acid catalysts may have a broad range of composition, porosity, density, type of acid groups and distribution of acid groups. Solid acid catalysts may be recovered and reused, optionally with a treatment to regenerate any activity that may have been lost in use. Some solid acid catalysts that may be used in the disclosed process include, but are not limited to Amberlyst 35, Amberlyst 36, Amberlyst 15, Amberlyst 131 (Rohm and Haas, Woodridge, Ill.), Lewatit S2328, Lewatit K2431, Lewatit S2568, Lewatit K2629 (Sybron Corp, Birmingham, N.J.), Dianion SK104, Dianion PK228, Dianion RCP160, RCP21 H, Relite RAD/F (Mitsubishi Chemical, White Plains, N.Y.), and Dowex 50WX4 (Dow Chemical).

One example of a solvent that may be used is a polar solvent. The polar solvent maybe a polar aprotic solvent. Examples of possible solvents include, but are not limited to, 1-methyl-2-pyrrolidinone, dimethylacetamide, dimethylformamide, dimethyl sulfoxide, methyl ethyl ketone, methyl isobutylketone, acetonitrile, propionitrile, and combinations thereof.

In certain embodiments of the method, over 40% of hexoses present in the starting reactants are converted to HMF, the percent conversion being calculated by molar yield as described below. Yield may be increased by altering any of the variables, such as solvent type, concentration, catalyst, time and/or temperature of the reaction conditions, etc. It has been further found that the gradual removal of water from the dehydration reaction increases the yield of HMF. The dehydration of fructose to HMF occurs with the loss of three water molecules, and the formation of three points of non-saturation, or double bonds (two alkene bonds, and the carbonyl group). By removing water as it is formed, side-reactions are thereby minimized, and an increased yield has been observed. Water removal may take place via evaporation. A rotary evaporation machine may be employed to promote water removal. The use of a rotary evaporator, or "rotovap," is well-known in the art. Water removal may also be carried out by evaporation from the reaction mixture and condensation as ice or water on a cold finger or reflux condenser. Water may also be removed by distillation, including azeotropic distillation with a water-entraining solvent which may optionally be stripped of water and the water depleted solvent returned to the reaction vessel. A suitable distillation apparatus, such as a Barrett type receiver may also be employed. A water-absorbing material may also be used to remove water. Such materials are well-known in the art, and include, but are not limited to, molecular sieves.

In one embodiment, the reactions disclosed herein are performed at moderately high temperatures, typically in a range of from about 95° to about 125° C. In a further embodiment, the temperature range is from about 105° C. to about 115° C. It is preferable to use temperatures below 200 degrees Celsius. The reactions disclosed herein typically occur in a time frame of from about one to about six hours. More typically, the reactions take from about two hours to about five and a half hours. If additional steps regarding the isolation and purification of HMF are preformed, additional time may be required.

As used herein, the term "zeolite" refers to a hydrated silicate of aluminum and one or both of sodium and calcium. Examples include, but are not limited to, analcite, chabazite, heulandite, natrolite, stilbite, thomsonite, in either powder or pellet form. Commercial zeolites products include, but are not limited to, CBV 3024 and CBV 5534G (Zeolyst International), T-2665, T-4480 (United Catalysis, Inc), LZY 64 (Union Carbide), and H-ZSM-5 (PQ Corporation).

As used herein, Cornsweet 90 refers to a high fructose corn syrup product of commerce nominally containing 60% to 70% fructose. High fructose corn syrup refinery intermediate and by-product is a fructose-rich stream generated in a fractionation system positioned after an isomerization column in the production of high fructose corn syrup. A suitable process stream from crystallizing fructose is called "mother liquor" and comprises a solution of fructose in ethanol. Typically this process stream is about 24% solids, almost all of the solids being fructose, and contains about 60% ethanol. For use in HMF production, the ethanol can be removed from the mother liquor. A similar mother liquor from glucose crystallization contains about 50% solids. Mixed carbohydrate sources can be obtained by blending carbohydrates, such as by adding crystalline fructose to high fructose corn syrup.

As used herein, "reaction yield" is calculated using the equation (moles of product/moles of starting material)*100. Product purity is reported on a weight percent basis.

As used in this equation, "starting material" refers to the fructose present in the carbohydrate source, mixed carbohydrate source, or other reactant for the particular dehydration reaction.

As used herein, the term "fructose source" refers to a material that comprises sucrose. Typical embodiments are solutions having at least 25% sucrose by solute weight, and which may include other materials such as other carbohydrate compounds. Preferably, the carbohydrate compounds are hexoses. The versatility of the reaction conditions provided herein allow an industrially convenient source to be used as the starting material, that is to say, the reaction is not limited to a particular carbohydrate source or to fructose of high purity.

Suitable fructose sources typically include high fructose corn syrup (HFCS) or any HFCS refining process stream that includes at least 25% sucrose. HFCS is typically commercially available in products comprising solutions having 42% to 95% fructose by solute weight which are typically sold for use as industrial scale sweeteners. The most economical embodiments of the invention use HFCS having about 90% sucrose by solute weight. However, less economical embodiment's invention can be practiced with sources having less sucrose by weight. To improve economic efficiencies, less pure sucrose sources can be conveniently blended with higher purity sucrose sources or even crystalline sucrose to achieve a solution having at least 25% sucrose by solute weight.

Optional neutralization of the product isolate is carried out by addition of a suitable alkali substance, such as a basic ion exchange resin, potassium hydroxide, or sodium hydroxide. This neutralization step allows for subsequent product recovery by distillation without heat-catalyzed degradation or polymerization, resulting in the elimination of tarry degradation products and resinous solids being formed in distillation. This neutralization step also allows for subsequent product recovery with a flowing agent without heat-catalyzed degradation or polymerization, resulting in the elimination of tarry degradation products and resinous solids being formed in distillation.

HMF can be purified from reaction mixtures by removal of catalyst resin and forming a product isolate, neutralizing the product isolate, removing solvent from product isolate by distillation, and treating the resulting distillant with water and an organic solvent. HMF partitions to the organic solvent and can be recovered with purity in excess of 95% by weight. This level of purity has not been obtained by other processes.

After HMF has been purified from reaction mixtures by removal of the solid acid catalyst and forming a product isolate, the solid acid catalyst may be rinsed with the organic solvent used to carry out the reaction to recover product contained within the catalyst. After the rinse, the solid acid catalyst may be reused in a subsequent reaction. In a preferred embodiment, after HMF has been purified from reaction mixtures by removal of the solid acid catalyst forming a product isolate, the solid acid catalyst may be rinsed with a second organic solvent to recover product contained with in the catalyst. After the rinse, the solid acid catalyst may be reused in a subsequent reaction.

Purity was determined by $^{13}C$ NMR and Proton NMR, in some cases by capillary GC, and in some cases by UV adsorption.

As used herein, the term "non-aqueous mixture" refers to a mixture comprising a non-aqueous solvent and at least one other component, wherein the content of the solvent is greater than the content of the at least one other component, as measured by volume. The at least one other component may comprise, without limitation, a water-containing substrate, such as HFCS, or an organic solvent. Non-aqueous solvents are usually measured by volume, and other components are usually measured by weight.

As used herein, the term "isolate" refers to the process of preservation of a material originally present in a product mixture after the product mixture has been subjected to a step to remove other material from the product mixture, as well as the isolated material resulting from the process. Examples of "other material" that is removed includes without limitation, solid material, such as catalyst by methods including, but not limited to, the processes of filtration, decantation, centrifugation, and washing. Filtration may be performed by one of the processes selected from the group comprising but not limited to gravity filtration, vacuum filtration, and suction filtration.

The term "non-volatile flowing agent" as used herein refers to an inert material which, when added to a product mixture, aids in the recovery of the desired compound by distillation. In certain embodiments, the fugacity of the flowing agent is sufficiently low so that it will not volatilize as the target product is removed by evaporation.

The formation of two immiscible solvent phases in the reaction mixture facilitates purification of an HMF product. Solvents can be easily classified on the basis of polarity. One such measure of polarity is the Log P value. Log P is defined as the partition coefficient of a given compound in a two-phase system of water and octanol. Log P can be determined experimentally or calculated from hydrophobic fragmental constants according to standard procedures (Hansch, C. & Leo, A (1979) *Substituent constants for correlation analysis in chemistry and biology*. John Wiley & Sons, New York N.Y.; Leo, A., Hansch, C. & Elkins, D. (1971) Chem. Rev. 71, 525;Rekker; R. F. (1977) *The hydrophobic fragmental constant*, Elsevier, Amsterdam; Rekker, R. F. & de Kort, H. M. (1979) Eur. J. Med. Chim. 14, 479).

Preferred two-phase organic solvent systems include a first solvent having a log P value of less then zero and a second solvent having a log P value in the range of about 0.4 to about 3.4; a further two-phase organic solvent systems include a first solvent having a log P value in the range of about −0.75 to about −1.95. In a further embodiment the second solvent has a log P value in the range of from about 0.6 to about 2.7, and in an additional embodiment, the two-phase organic solvent systems include a first solvent having a log P value of about −1.04 and a second solvent having a log P value of about 1.32. A suitable two-phase organic solvent system comprises a first phase of dimethylformamide and a second phase of methyl isobutyl ketone. Table 1 provides Log P data for certain solvents.

Methyl isobutyl ketone is generally miscible with a broad range of solvents (J. S. Drury (1952) *Miscibility of solvent pairs*, Industrial and Engineering Chemistry 44:11, page C-684). Solvents immiscible with methyl isobuyl ketone include diethanolamine, ethylene glycol, glycerol and triethylene glycol. None of these solvents are suitable for the intended reaction because of their reactivity.

TABLE 1

Log P data for some solvents

| Solvent | Log P* |
|---|---|
| 1, 2-Dichlorobenzene | 3.38 |
| Carbon tetrachloride | 2.83 |
| Toluene | 2.69 |
| Chloroform | 2.24 |
| Benzene | 2.03 |
| 2-Heptanone | 1.83 |
| Butyl acetate | 1.71 |
| 1,2-Dichloroethane | 1.48 |
| Methyl isobutyl ketone | 1.32 |
| Dichloromethane | 1.25 |
| Ethyl propionate | 1.21 |
| 2-Pentanone | 0.91 |
| Diethyl ether | 0.89 |
| t-Amyl alcohol | 0.89 |
| Butanol | 0.88 |
| Cyclohexanone | 0.81 |
| Ethyl acetate | 0.66 |
| Pyridine | 0.64 |
| Tetrahydrofuran | 0.46 |
| 2-Butanone | 0.29 |
| 2-Propanol | 0.05 |
| Acetone | −0.24 |
| Dioxane | −0.27 |
| Ethanol | −0.32 |
| Acetonitrile | −0.34 |
| Methanol | −0.77 |
| N, N-Dimethylformamide | −1.04 |
| Dimethyl sulfoxide | −1.35 |
| Formamide | −1.51 |
| Ethylene glycol | −1.93 |

*Log P values were taken from Hansch, C. & Leo, A (1979) Substituent constants for correlation analysis in chemistry and biology. John Wiley & Sons, New York NY; Leo, A., Hansch, C. & Elkins, D. (1971) Chem. Rev. 71, 525.

It has also been surprisingly found that other furan derivatives, particularly HMF ethers may be synthesized using the methods of the present invention with slight variations. Generally, ethers may be formed from any R group, such as alkyl, cycloalkyl, allyl, aryl and the like. Such variations include but are not limited to the introduction of alcohol having the appropriate constituent R group, such as, for example, ethanol (EtOH) where R is $C_2H_5$, as a polar solvent in either batch reactions or via column elution. This method would therefore comprise: i) combining materials comprising a fructose source, an alcohol solvent, and a catalyst to form a reaction mixture; ii) heating said reaction mixture to a temperature and for a time sufficient to promote an acid-catalyzed dehydration reaction of the fructose in the fructose source to form a product mixture; and iii) isolating an ether derivative from said product mixture. HMF ethers, such as ethoxymethylfurfural (EMF), are more stable than HMF because they lack the exposed hydroxyl group of HMF. EMF is shown in the structure below:

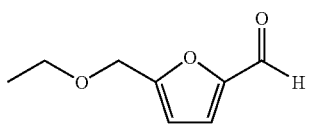

In an embodiment the fructose source is a HFCS. The use of a column in the synthetic process enables a continuous flow of heated fructose solution, thereby decreasing the amount of polymerization and by-product formation. Further distillation may also be performed to purify EMF from the product mixture. The use of column elution creates a continuous flow and is a fairly simple process that efficiently leads to a more stable product. The subsequent purification via distillation is also a simple process that is economically feasible. Furthermore, yields have been surprisingly high, in the range of 85-100%. Purification may also be used in the form of liquid or gas chromatography.

It has also been surprisingly found that levulinic acid may be efficiently synthesized from a carbohydrate source primarily including fructose. Levulinic acid is shown in the structure below:

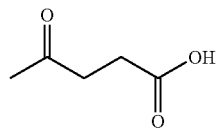

The method comprises combining a fructose source, such as high-fructose corn syrup, with a polyethylene glycol and an acidic resin to form a reaction mixture. The reaction mixture is then heated with constant, or continuous stirring to a temperature and for a time necessary to promote the reaction and form a product mixture. Levulinic acid is then isolated from the product mixture. A polyethylene glycol block can be seen in the structure below:

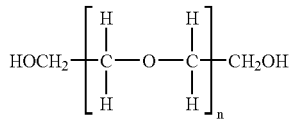

The use of end-capped polyethylene glycol material has been surprisingly efficient as it eliminates the formation of undesirable PEG-HMF ethers. As recognized by one of ordinary skill in the art, an end-capped glycol has the forgoing structure except that the terminal hydroxyl groups are substituted with an alkyl or ether group.

Another method of making levulinic acid from a fructose source involves heating a mixture of high-fructose corn syrup and water with an acidic ion exchange resin catalyst. This reaction normally proceeds in a temperature range of 100-150° C., and has surprisingly been found to produce levulinic acid in high yields. This method provides substantial improvement over the known method of using zeolites as catalysts in synthesizing levulinic acids.

In another embodiment, a method of preparing 2,5-bis-(hydroxymethyl)furan is disclosed. The method includes heating a reaction mixture comprising 2,5-(hydroxymethyl)furaldehyde, a solvent, and a catalyst system comprising nickel and zirconium at a temperature, for a time, and at a pressure sufficient to promote reduction of the 2,5-(hydroxymethyl)furaldehyde to 2,5-bis-(hydroxymethyl)furan to produce a product mixture comprising 2,5-bis-(hydroxymethyl)furan. In an embodiment, the reaction mixture comprising 2,5-(hydroxymethyl)furaldehyde is a crude reaction mixture.

As used herein, the term "crude reaction mixture" refers to an unrefined or unpurified composition.

EXAMPLES

The following are examples of the dehydration of a fructose source to a furan derivative or organic acid, as well as isolation and/or purification techniques to optimize product recovery of increased product yield. The examples are not meant to limit the scope of the invention, as defined by the claims.

Example 1

Preparation of HMF from High Fructose Corn Syrup at 115° C. in N-Methylpyrrolidinone (NMP)

A 250 mL 3-neck round bottom flask was fitted with a magnetic stir bar, heating mantle, reflux condenser, and temperature probe. To this flask was charged 100 mL of NMP (Aldrich) and 20 g of Amberlyst 35 resin (Rohm and Haas, Woodridge, Ill.). Amberlyst 35 is a macroreticular, strongly acidic, polymeric catalyst. The mixture was heated to 115° C., and 50 g of Cornsweet 90 (HFCS, ADM, Clinton Iowa) was added. Heating continued in this manner at 115° C. over a 5 hour period. Water condensed on the reflux condenser. After 5 hours, the contents of the flask were cooled to about 70° C., and the resin removed by vacuum filtration to provide a product isolate. The product isolate was analyzed to provide a solution of 14.2% HMF by weight and 4.7% fructose. Calculations indicate an 80.6% molar yield of HMF from fructose and 94.1% conversion.

Example 2

Preparation of HMF from High Fructose Corn Syrup at 105° C. in NMP

This example illustrates the effect of temperature on the dehydration of fructose to HMF. A 250 mL 3-neck round bottom flask was fitted with a magnetic stir bar, heating mantle, reflux condenser, and temperature probe. To this flask was charged 100 mL of NMP (Aldrich) and 20 g of Amberlyst 35 resin (Rohm and Haas, Woodridge, Ill.). The mixture was allowed to heat to 105° C., and 50 g of Cornsweet 90 (HFCS, ADM, Clinton, Iowa) was added. Heating continued in this manner at 105° C. over a 5 hour period. Water condensed on the reflux condenser. After 5 hours, the contents of the flask were cooled to about 70° C., and the resin removed by vacuum filtration to provide a product isolate. The product isolate was analyzed to provide a solution of 12.9% HMF and 3.9% fructose. Calculations indicate a 71.6% molar yield of HMF from fructose and 85.4% conversion.

Example 3

Preparation of HMF from High Fructose Corn Syrup at 105° C. in NMP Under Vacuum Conditions This example illustrates the effect of distillation on the dehydration of fructose to HMF. A 250 mL 3-neck round bottom flask was fitted with a magnetic stir bar, heating mantle, condenser, temperature probe, and receiving flask. To this flask was charged 100 mL of NMP (Aldrich), 20 g of Amberlyst 35 resin (Rohm and Haas, Woodridge, Ill.), and 50 g of Cornsweet 90 syrup. The mixture was heated to 105° C. under house vacuum. The distillate was collected. After 2 hours, the contents of the flask were cooled to about 80° C., and the resin removed by vacuum filtration to provide a product isolate. The product isolate was analyzed to provide a solution of 14.2% HMF and 1.1% fructose. Calculations indicate a 75.7% molar yield of HMF from fructose and 79.5% conversion.

Example 4

Preparation of HMF from High Fructose Corn Syrup at 115° C. in NMP

This example illustrates the effect of distillation on the dehydration of fructose to HMF. A 2 L 3-neck round bottom flask was fitted with a magnetic stir bar, heating mantle, condenser, temperature probe, and receiving flask. To this flask was added 500 mL of NMP (Aldrich), 200 g of Amberlyst 35 wet resin (Rohm and Haas, Woodridge, Ill.), and 500 g of Cornsweet 90. The mixture was heated to 115° C. and subjected to vacuum distillation under house vacuum. After 4 hours, the resin was removed by filtration to provide a product isolate of 729.68 g of 20.4% HMF. Calculations indicate a 68.6% yield of HMF.

Example 5

Preparation of HMF from High Fructose Corn Syrup at 105° C. in DMAc

This example illustrates the effect of solvent on the dehydration of fructose to HMF. A 250 mL 3-neck round bottom flask was fitted with a magnetic stir bar, heating mantle, reflux condenser, and temperature probe. To this flask was charged 100 mL of DMAc (Aldrich) and 20 g of Amberlyst 35 resin (Rohm and Haas, Woodridge, Ill.). The mixture was heated to 105° C., and 50 g of Cornsweet 90 (HFCS, ADM, Clinton, Iowa) was added. Heating was continued in this manner at 105° C. over a 5 hour period. Water was condensed on the reflux condenser. After 5 hours, the contents of the flask were cooled to about 90° C., and the resin was removed by vacuum filtration to provide a product isolate. The product isolate was analyzed to provide a solution of 13.5% HMF and 6.0% fructose. Calculations indicate 62.1% molar yield of HMF from fructose and 74.6% conversion.

Example 6

Preparation of EMF from Fructose in Batch Mode

A 500 mL round bottom flask equipped with a reflux condenser, temperature probe, and magnetic stir bar was charged with a solution of 30 g fructose (Aldrich), 225 mL HPLC grade ethanol (Aldrich), and 30 g of Amberlyst 131 resin (Rohm and Haas). Amberlyst 131 is a strongly acidic polymeric catalyst with a particle size of 0.7-0.8 mm and water content of 65%. The stirred mixture was heated to reflux for 24 hours. At this time, the slurry was filtered and the resin washed with ethanol to provide 174 mL of product isolate containing 5.4 g/L HMF and 61.6 g/L EMF.

Example 7

Preparation of EMF from Fructose via Column Elution

A 100 mL glass liquid-chromatography column (2.54 cm I.D) was slurry packed in HPLC grade ethanol (EtOH) with Amberlyst 131 resin obtained from Rohm and Haas Company (Woodridge, Ill.). The resin was washed with 500 mL of EtOH. The final packed volume was 100 ml. The feed material consisted of 5 mL of a 20% solution of fructose in EtOH.

The feed was then loaded on the resin column by gravity flow and fractions were eluted. The column was maintained at 60° C. and elution at 0.6 mL/min. Table 2 summarizes the results of this study. A complete conversion of fructose to a mixture of HMF/EMF was achieved, with the major product being EMF.

TABLE 2

Column Synthesis of EMF from Fructose using Amberlyst 131 Resin.[1]

| Fraction # | Volume (mL) | Fructose (ppm) | HMF (ppm) | EMF (ppm) |
|---|---|---|---|---|
| 2 | 8 | 0 | 0 | 0 |
| 5 | 13.6 | 0 | 0 | 0 |
| 7 | 21.6 | 0 | 0 | 294 |
| 9 | 32.1 | 262 | 370 | 1,862 |
| 11 | 40.1 | 79 | 420 | 2,613 |
| 13 | 48.1 | 134 | 364 | 4,451 |
| 15 | 57.1 | 119 | 794 | 6,008 |
| 17 | 65.6 | 120 | 615 | 6,385 |
| 19 | 73.6 | 0 | 308 | 4,293 |
| 21 | 82.1 | 0 | 0 | 1,488 |
| 24 | 94.1 | 0 | 0 | 276 |
| 26 | 102.1 | 0 | 0 | 60 |

[1]Column was maintained at 60° C. with a steady flow rate of 0.6 mL/min.

Example 8

Preparation of EMF from Fructose via Column Elution

This example illustrates the effect of charge in resin to Amberlyst 35 obtained from Rohm and Haas Company (Woodridge, Ill.). Amberlyst 35 is a macroreticular, strongly acidic, polymeric catalyst. The feed material was prepared and loaded on to the column by gravity flow as described in Example 7. The column was maintained at 60° C. and the elution was carried out at 0.6 mL/min. A summary of this is provided in table 3. Nearly 85% of the starting fructose was converted into a mixture of HMF/EMF with the major product being EMF.

TABLE 3

Column Synthesis of EMF from Fructose using Amberlyst 35 Resin.[1]

| Fraction # | Volume (mL) | Fructose (ppm) | Ethyl Levulinate (ppm) | HMF (ppm) | EMF (ppm) |
|---|---|---|---|---|---|
| 1 | 2.0 | 263 | 242 | 263 | 263 |
| 3 | 13.0 | 271 | 249 | 271 | 271 |
| 5 | 25.0 | 230 | 212 | 230 | 230 |
| 7 | 34.5 | 253 | 233 | 253 | 253 |
| 8 | 37.5 | 227 | 209 | 227 | 579 |
| 10 | 46.5 | 2,737 | 948 | 1,180 | 5,687 |
| 12 | 58.0 | 2,507 | 203 | 1,157 | 7,844 |
| 14 | 67.0 | 1,970 | 1,526 | 1,186 | 9,526 |
| 16 | 76.0 | 520 | 246 | 325 | 2,023 |
| 18 | 85.0 | 282 | 260 | 282 | 282 |
| 19 | 89.5 | 256 | 236 | 256 | 256 |
| 20 | 96.5 | 269 | 248 | 269 | 269 |

[1]Column was maintained at 60° C. with a steady flow rate of 0.6 mL/min.

Example 9

Process for the Synthesis and Purification of EMF

Dehydration: Amberlyst 131 Wet (145 g) was dried in vacuum at 85° C. for three days. This catalyst was combined with 117 g crystalline fructose and 468 g of 100% ethanol in a steel reactor. With stirring at 600 rpm, the reaction mixture was gradually heated to 110° C. over 30 minutes. The temperature was maintained for 45 minutes, and then the reaction mixture was cooled to ambient temperature over 7 minutes. The catalyst was filtered from the red-black reaction mixture, and the reaction mixture was treated with a rotary evaporator under house vacuum to remove ethanol.

Distillation of EMF on Wined-Film Evaporator: Poly(ethylene glycol)-400 (47 g) was added to the dark residue (89 g). EMF was distilled from this mixture on a wiped-film evaporator at 110° C., 4.7 mm Hg, and 400 rpm, yielding a yellow distillate (68 g) containing EMF (44 g, 44% molar yield from fructose), ethyl levulinate (20 g, ELA), and ethanol (5 g). NMR (δ, 1H): 9.54, (s, 0.8 H) EMF; 7.16, (d, 1.0 H), EMF; 6.46, (s, 1.0 H), EMF; 4.46, (s, 2.0 H), EMF; 4.05, (quartet, 1.0 H) ELA; 3.63, (quartet, 0.7 H), EtOH; 3.52, (quartet, 2.0 H), EMF; 2.68, (t, 1.1 H), ELA; 2.49, (t, 1.2 H), ELA; 2.12, (s, 1.6 H), ELA; 1.17, (m, 5.6 H), ELA, EMF, EtOH.

Example 10

Preparation of HMF from Fructose Using a Two-Phase Organic Solvent System

A 500 mL round bottom three neck flask was equipped with a reflux-condenser, temperature probe, and a magnetic stir bar. To this flask was added 5 g of fructose, 5 g of Amberlyst 35 resin, and a first organic solvent comprising 50 mL of dimethylformamide (DMF) and a second organic solvent comprising 200 mL of methyl isobutyl ketone (MIBK). The reaction was heated to 85° C. for 7 h. The mixture was cooled and filtered. The resin was washed with small quantities of MIBK. The two layers were separated and the product isolate (155 mL) in the MIBK phase contained 17.9 g/L HMF to provide an overall yield of 89.3%.

Example 11

Reparation of Levulinic Acid from High Fructose Corn Syrup Using Acidic Resin Catalysts A 250 mL round bottom three neck flask was equipped with a reflux-condenser, temperature probe, and a magnetic stir bar. To this flask was added 50 g of Cornsweet 90 syrup, 20 g of Amberlyst 35 resin, and 100 mL of poly(ethyleneglycol) dimethyl ether-500. The mixture was heated to 100° C. for 4 h. The mixture was cooled and filtered to provide an overall yield of 45.3% levulinic acid.

Example 12

Preparation of Levulinic Acid from Fructose Using Acidic Resin Catalysts

A solution of crystalline fructose (30 g, 90%) in water (500 mL) was placed in a 1 L autoclave reactor. To this reactor was added 60 g of Amberlyst 35 Wet resin. The solution was stirred (500 rpm) and heated to 150° C. After 4.5 hours, the reactor was cooled and the solution was filtered to remove the catalyst to provide a product isolate. The dark brown product isolate (72.04 g) contained 149.83 g/kg levulinic acid to provide an overall yield of 62% levulinic acid from fructose.

Example 13

Preparation of Levulinic Acid from High Fructose Corn Syrup Using Acidic Resin Catalysts A solution of Cornsweet 90 (45.24 g) in water (500 mL) was placed in a 1 L autoclave reactor. Amberlyst 35 Wet resin (60 g) was added and the mixture stirred (500 rpm). After 18 hours, the reactor was cooled and the solution filtered to provide a product isolate. The product isolate was treated with a rotary evaporation machine to remove the solvent, and provided 17.98 g of dark brown oil containing 467.22 g/kg levulinic acid for a yield of 41.2%.

Example 14

Process for the Preparation and Purification of HMF from HFCS

Step 14a. Neutralization: A 202.7 g sample of product isolate prepared as described in Example 4 was placed in a 500 mL Erlenmeyer flask, and 25.0 g of poly(ethylene glycol)-600 was added to serve as a flowing agent in later purification. The mixture was stirred continuously for 30 minutes at ambient temperature and neutralized with the gradual addition of Amberlyst A26OH resin (Rohm and Haas) before being subjected to distillation to remove solvent. Amberlyst A26OH is a strong base, type 1, anionic, macroreticular polymeric resin. The pH of the crude product mixture was increased to 7.5-8.0 by the application of Amberlyst A26OH resin. The Amberlyst A26OH resin was then removed by filtration.

Step 14b. Distillation of DMAc: The solvent (DMAc) was distilled from the neutralized product mixture under vacuum (4-6 torr) at 100° C. using a 4" Vigreaux column with six tiers. A brown residue containing HMF and poly(ethylene) glycol (64.5 g, 28.8% HMF) remained in the distillation vessel and 150 g of distilled DMAc were isolated.

Step 14c. Short Path Distillation of HMF: The brown residue containing HMF (145.5 g, 28.8% HMF) obtained from fractional distillation in step 14b was subjected to short path distillation at 150° C. and 0.014-0.021 torr. A yellow distillate (96% purity-HMF, 47.4 g) and brown residue (79.6 g) were isolated. The distillate crystallized upon cooling. NMR ($\delta$, 1H): 9.49, (s, 1 H); 7.16, (d, 1.0 H); 6.46, (s, 1.0 H); 4.62, (s, 2.0 H).

Regeneration of PEG for re-use: A 12.5 g portion of the dark brown PEG residue obtained from the short path distillation was treated with 50 mL of hot water and 24 g of carbon (Calgon, CPG-LF 12X40). NMR indicated that the dark brown PEG residue was composed of greater than 95% PEG. The mixture was allowed to stir for three days. The mixture was vacuum filtered to remove the carbon and 8.4 g of a clear yellow oil resembling the starting PEG in appearance was isolated. NMR indicated that the purity of the recovered PEG was 100%.

Example 14a

Process for the Purification of HMF from HFCS

A 180 g sample of material prepared and neutralized as described in Example 4 was added to 20 g poly(ethylene glycol) dimethyl ether-500 flowing agent. This material was subjected to short path distillation at 150° C. and 5 mbar. A yellow distillate (67.4% purity HMF, 11.92 g) and brown residue (191 g) were isolated.

Example 15

Process for the Purification of HMF from HFCS

Step 15a. Neutralization: An HMF product isolate as prepared in example 4 was neutralized with the gradual addition of aqueous sodium hydroxide (pH 7.5) before being subjected to distillation to remove solvent.

Step 15b. Fractional Distillation to remove NMP: The neutralized product isolate was subjected to distillation under reduced pressure (4-6 torr) at 115° C. using a 4" Vigreaux column with six tiers to remove solvent (NMP). A purified product isolate comprising a brown residue (264.6 g) and 490 g of distilled NMP were obtained.

Step 15c. Solvent Extraction: A 30.25 g sample of purified product isolate (brown residue prepared in step 15b), 45 mL of ethyl acetate, and 15 mL of water were placed in a 125 mL Erlenmeyer flask and allowed to stir at ambient temperature. After 20 min, the mixture was transferred to a separatory funnel and the two layers separated. The ethyl acetate layer was removed and the aqueous layer was washed with 20 mL of ethyl acetate, the organic layers were combined and dried over $MgSO_4$. The dried combined organic layer was filtered and the solvent evaporated to provide 15.91 g of bright red oil which was 84.2% purity HMF.

Example 16

Process for the Purification of HMF from HFCS

Solvent Extraction: A 37.4 g sample of the solvent stripped material prepared as described in Example 15, 47 mL of methyl isobutylketone (MIBK), and 9.6 mL of water were placed in a 125 mL Erlenmeyer flask and allowed to stir at ambient temperature. After 20 min, the solution was transferred to a separatory funnel and the two layers separated. The aqueous phase was washed with 20 mL of MIBK and the organic phases combined and dried over $MgSO_4$. The solution was filtered and the solvent evaporated to provide 24.33 g of bright red oil which was 88% purity HMF in 97% yield.

Example 17

Process for the Preparation and Purification of HMF from Fructose

Step 17a. Dehydration: Amberlyst 35 Dry (20 g) was combined with 40 g crystalline fructose and 200 mL of acetonitrile (ACN) in a three neck flask equipped with a reflux condenser, temperature probe, and magnetic stir bar. The reaction mixture was heated to flux (80° C.). The temperature was maintained for 5 hours, and then the reaction mixture was cooled. The catalyst was filtered and washed with acetonitrile to provided a product isolate. The product isolate was subjected to rotary evaporation to provide for evaporation of the solvent and 17.6 g of brown oil containing 33.9% HMF.

Step 17b. Chromatographic Purification of HMF from ACN Reaction Mixture: A glass-liquid chromatography column (2.54 cm I.D) was packed in heptane with C-Gel 560, 60-200µ silica (Uetikon, Switzerland). The feed material for chromatographic separation using silica gel was prepared by dissolving the dehydration product (2.95 g) in 10 mL of 80:20 heptane:acetone solution. The feed material was loaded on the silica column by gravity flow and fractions were eluted including those shown in Table 3.

TABLE 4

Chromatographic Purification of HMF from Crude ACN Reaction Mixture.[1]

| Fraction # | Fructose | Fructose (ppm) | HMF (ppm) | Formic Acid (g/kg) | Levulinic Acid (g/kg) |
|---|---|---|---|---|---|
| 1 | 10 | 967 | 23,239 | 0.70 | 0.00 |
| 5 | 4 | 384 | 476,872 | 1.53 | 5.38 |
| 7 | 0 | 0 | 826,108 | 0.00 | 0.00 |
| 8 | 0 | 0 | 814,378 | 0.00 | 11.59 |
| 9 | 0 | 0 | 622,706 | 0.00 | 17.62 |
| 10 | 22 | 2215 | 101,450 | 0.00 | 43.26 |
| 11 | 14 | 1386 | 70,241 | 0.00 | 15.22 |
| 12 | 13 | 1264 | 90,195 | 0.00 | 11.93 |
| 13 | 23 | 2252 | 40,207 | 4.03 | 12.14 |
| 14 | 28 | 2782 | 20,817 | 7.30 | 8.84 |
| 15 | 25 | 2521 | 30,723 | 9.20 | 1.05 |
| 16 | 35 | 3457 | 23,024 | 0.00 | 0.00 |
| 17 | 58 | 5847 | 26,892 | 20.66 | 0.00 |
| 18 | 88 | 8799 | 38,819 | 12.46 | 0.00 |
| 19 | 128 | 12837 | 32,050 | 8.66 | 0.00 |
| 20 | 116 | 11590 | 33,163 | 22.43 | 0.00 |

[1]Samples were eluted from C-Gel 560, 60-200 microns using heptane: acetone gradient system.

Hence, by gradient elution of the column, isolated fractions with HMF content of >81% were obtained.

Example 18

Process for the Purification of HMF

A 2.0 g sample of HMF (21%) was prepared in as in the dehydration Step 17a. of Example 17 using HFCS, treated with MIBK (2 mL) and water (1 mL), and the layers were separated. The organic layer was dried over $MgSO_4$, filtered, and the solvent evaporated to provide a bright red extract of 78.9% HMF purity with 93.9% recovery of HMF from the crude material.

Example 19

Preparation of HMF from HFCS Using Acidic Resin Catalysts at 115° C.

This example illustrates the effect of resin on the dehydration of fructose to HMF. A summary of data is shown in Table 5. A 250 mL 3-neck round bottom flask was fitted with a magnetic stir bar, heating mantle, reflux condenser, and temperature probe. To this flask was charged 50 mL of NMP (Aldrich), 50 g of polyethylene glycol dimethyl ether-600, and 50 g of HFCS. The mixture was allowed to heat to 65° C., and 20 g of Dianion RCP160M resin (Mitsubishi Chemical America, Inc.) was added. Dianion RCP160M resin is a strongly acidic polymeric catalyst with a particle size distribution of 250-710 μm and a water retention of 45-55%. Heating continued in this manner at 115° C. over a 4 hour period. Water condensed on the reflux condenser. After 4 hours, the contents of the flask were cooled to about 90° C., and the resin removed by vacuum filtration to provide a product isolate. The product isolate was analyzed and found to be a solution of 17.5% HMF and 0.2% fructose. Calculations indicate 74.5% molar yield of HMF from fructose and 77.1% conversion.

TABLE 5

Comparison of HMF Conversion with Various Resins.[1]

| Reference # | Time (h) | Resin | HMF Yield (%) | Conversion (%) |
|---|---|---|---|---|
| 4474-58 | 1 | RAD/F | 54.1 | 60.1 |
|  | 2 | RAD/F | 63.5 | 67.3 |
| 4474-59 | 1 | RCP160M | 61.2 | 63.9 |
|  | 2 | RCP160M | 74.5 | 77.1 |
| 4474-29 | 1 | Amberlyst 35 | 34.6 | 46.9 |
|  | 2 | Amberlyst 35 | 57.1 | 70.2 |

[1]Reactions were performed with HFCS, in NMP/PEGE at 115° C.

Example 20

Process for the Preparation and Purification of HMF from HFCS

A 10 g sample of solvent stripped material as prepared in Example 15, step 15b (42% HMF purity) was placed in 50 mL of distilled water and 10 g of an inert adsorbent (Calgon CPG 12X40 carbon) was placed in a beaker and allowed to stir at room temperature for 12 hours. HMF adsorbs light at 284 nm. UV analysis ($\lambda$=284 nm) after 12 hours of stirring indicated HMF had been adsorbed from the mixture. The carbon was collected by filtration, washed with water, and then allowed to stir at room temperature in 50 mL of acetone to desorb HMF. After 12 hours, the carbon was removed by filtration and the filtrate evaporated to provide 3.31 g of material with 80.1% HMF purity.

Example 21

Process for the Preparation and Purification of HMF from HFCS

A 33.0 g sample of solvent stripped material as prepared in Example 15 (42% HMF purity) was treated with 35 g of an inert adsorbent (Calgon CPG 12X40 carbon) in 165 mL of distilled water. The mixture was allowed to stir at room temperature for 12 hours. The carbon was removed by Buchner filtration, rinsed with water, and dried under vacuum. The dried carbon was subjected to Soxhlet extraction using 600 mL of acetone for 18 hours to desorb HMF. The solvent was evaporated to provide 18.41 g of deep red oil having an HMF purity of 67.1%. The total recovery of HMF was 90.1%.

Example 22

Preparation of HMF from HFCS Using Rotary Evaporation

This example illustrates the effect of rotary evaporation on the dehydration of fructose to HMF. To a 500 mL round bottom flask was charged 100 mL of NMP (Aldrich), 25 g of high-fructose corn syrup, and 15 g of wet Amberlyst 35 resin. An oil bath was heated to 120° C., and the flask rotated in the bath, under vacuum of 200 mm Hg. Rotary evaporation continued in this manner at 120° C. over a 1 hour period. Distillate was collected. After 1 hour, the contents of the flask were subjected to Buchner filtration to remove the resin to provide a product isolate. The product isolate was analyzed to show 7.1% HMF, 91.5% NMP, and 1.9% water. Calculations indicate 88.6% molar yield of HMF from HFCS and 90.7% conversion.

Example 23

Preparation of HMF from HFCS with Molecular Sieves

This example illustrates the usefulness of molecular sieves as drying agents in the production of HMF from HFCS. To a 3-neck 500 round bottom flask equipped with a condenser, temperature probe, and stirring bar, was added 100 mL of NMP, 50 g of HFCS, 20 g of wet Amberlyst 35 resin, and 20 g of UOP 3A molecular sieves. The reaction was heated to 105° C. and let stir under these conditions for 1 hour. Results indicate a 10.6% HMF solution providing an overall yield of 60.6%. The addition of sieves to promote the removal of water during the reaction allows for a faster conversion of HFCS to HMF.

Example 24

Preparation of HMF with Gradual Addition of HFCS to Reaction Mixture

This example illustrates the effect of gradual addition of HFCS to a heated reaction mixture. A 3-neck 500 mL round bottom flask was fitted with a dropping funnel, temperature probe, and a jacketed condenser with distilling head. To this flask was added 100 mL of NMP and 40 g of wet Amberlyst 35 resin. The flask was heated to 130° C. with vacuum and the feed material (100 g of HFCS in 50 mL of NMP) was added dropwise over 1.5 hours. Upon complete addition of the feed, the reaction continued with vigorous stirring for 3 hours. At this time, the reaction was cooled to 90° C., and the resin removed via Buchner filtration (#415 VWR paper) to provide a product isolate. Results indicate a product isolate of 10.4% HMF, 85.4% NMP, and 2.76% water. Thus, a 77.8% molar yield of HMF was obtained.

Example 25

Preparation of 2,5-bis-(hydroxymethyl)furan (FDM) from Crude HMF Reaction Mixture The sample of HMF material (30.01 g, 66% HMF) was placed in a 1 L Parr reactor vessel with ethyl acetate (350 mL) and 2.0 g of G-69B. G-69B is a powdered catalyst obtained from Sud-Chemie, Louisville, Ky., containing nominally 62% Nickel on Kieselguhr, with a Zirconium promoter, and has an average particle size of 10-14 microns. The vessel was purged 3×500 psi hydrogen with vigorous stirring (1000 rpm). The pressure was then maintained at 1250-1050 psi with heating to 150° C. for 1 hour. The reaction was allowed to cool and the catalyst removed by filtration. The solvent was removed by rotary evaporation to provide 27.32 g of brown liquid that solidified on cooling. TLC analysis indicated the complete conversion of HMF to FDM. $^1$H NMR data reveal a high purity product (>90%). The overall yield of FDM from HMF is 100%. GC/MS data revealed complete conversion of HMF to FDM m/z=128, 111, 97.

Example 26

Preparation of 2,5-bis-(hydroxymethyl)furan (FDM) from Crude HMF Reaction Mixture The sample of HMF material (46.09 g, 45% HMF) was placed in a 1 L Parr reactor vessel with ethyl acetate (350 mL) and 6.15 g of G-69B. The vessel was purged 3×500 psi hydrogen with vigorous stirring (1000 rpm). The pressure was then maintained at 1350 psi with heating to 150° C. for 1 hour. The reaction was allowed to cool and the catalyst removed by filtration. The solvent was removed by rotary evaporation to provide 18.48 g of brown solid. $^1$H NMR and gc/ms data reveal a high purity product (>95%). The overall yield of FDM from HMF is 90%. NMR (δ, 1 H): 4.54 (s, 2.0 H); 6.20 (s, 1.0 H).

What is claimed is:

1. A method of preparing an R-oxymethylfurfural ether of hydroxylmethylfurfural of the formula:

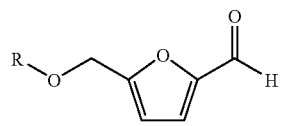

where R is selected from the group consisting of alkyl, cycloalkyl, and allyl, comprising:
   combining a fructose source and an R-OH solvent to form a reaction mixture and contacting the reaction mixture with a solid acid catalyst bed in a chromatographic column;
   heating the reaction mixture in the chromatographic column to a temperature and for a time sufficient to promote an acid-catalyzed dehydration reaction of fructose in the fructose source and to form R-oxymethylfurfural in a product mixture in the column; and
   simultaneously chromatographically separating the product mixture in the column to at least partially separate the R-oxymethylfurfural from other components of the product mixture and elute an enriched fraction containing the R-oxymethylfurfural from the column.

2. The method of claim 1 wherein the R-OH solvent is ethanol and the R-oxymethylfurfural is ethoxymethylfurfural.

3. The method of claim 1 wherein the acid catalyst is an acidic ion exchange resin.

4. The method of claim 1 wherein the fructose source is a mixed fructose source.

5. The method of claim 1 wherein the method further includes distilling the enriched fraction to further purify the R-oxymethylfurfural.

6. The method of claim 1, wherein the yield of the R-oxymethylfurfural is in the range of 85-100%.

7. The method of claim 1 wherein the reaction mixture consists essentially of the fructose source and the R-OH solvent in contact with the solid acid catalyst.

8. The method of claim 1 wherein the column is eluted with the R-OH solvent of the reaction mixture.

9. The method of claim 1 wherein the reaction mixture consists essentially of the fructose source and the R-OH solvent in contact with the solid acid catalyst and the column is eluted with the R-OH solvent of the reaction mixture.

* * * * *